United States Patent [19]

Meek et al.

[11] Plant 4,529

[45] Apr. 29, 1980

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 966,289

[22] Filed: Dec. 4, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A daisy capitulum type of chrysanthemum plant which is a sport of the cultivar Superstar, disclosed in U.S. Plant Pat. No. 4,299, granted Sept. 12, 1978. Yellow Superstar is distinguished from the parent cultivar by its medium yellow ray floret color.

1 Drawing Figure

The present invention comprises a new and distinct cultivar of *Chrysanthemum morifolium,* Ramat., hereinafter referred to by the cultivar name of Yellow Superstar.

Yellow Superstar is a product of planned sport induction program which had the objective of expanding the color range of the parental cultivar Superstar, disclosed in U.S. Plant Pat. No. 4,299, granted Sept. 12, 1978.

Yellow Superstar was discovered and selected by William E. Duffett and Jack M. Meek on Mar. 22, 1977 as two plants within a flowering block of Superstar in a controlled environment in Barberton, Ohio. Plants within the flowering block were derived from stock plants which had been irradiated as rooted cuttings with an x-ray source of 2600 r units.

The first act of asexual reproduction of Yellow Superstar was accomplished when vegetative cuttings were taken from the initial selection in August, 1978 in a controlled environment in Salinas, Calif. by a technician working under formulations established and supervised by William E. Duffett and Jack M. Meek. Continued asexual reproduction by vegetative cuttings for evaluative tests in flowering and stock programs in conjunction with horticultural examination of selected units initiated Apr. 20, 1978 has demonstrated that the combination of characteristics as herein disclosed for Yellow Superstar are firmly fixed and are retained through successive generations of asexual reproduction.

Yellow Superstar has not been observed under all possible environmental conditions. The phenotype may vary significantly with variations in environment such as temperature, light intensity and daylength. The following observations, measurements, and comparisons describe plants grown in Salinas, Calif. under greenhouse environmental conditions which approximate those generally used in commercial practice.

The following traits have been repeatedly observed and are determined to be basic characteristics of Yellow Superstar which in combination distinguish this chrysanthemum as a new and distinct cultivar.

(1) Daisy capitulum type.

(2) Flat capitulum form.

(3) Medium yellow ray floret color.

(4) Diameter across face of inflorescence ranging from 100 to 120 mm. at maturity.

(5) Uniform seven week photoperiodic flowering response to short days.

(6) Tall plant height (requires 1 to 2 long day weeks prior to short days to attain a flowered plant height of 72 to 82 cm. when grown as a non-pinched plant for April through November flowerings).

(7) Semi-upright branching pattern.

(8) Yellow green (immature) to yellow (mature) disc floret color.

The accompanying color photographic drawing shows typical inflorescence and foliage characteristics of Yellow Superstar. Some difficulty was encountered in obtaining accurate color representation, with the rendition being more red and less yellow than the actual flower color of Yellow Superstar. The color readings in the following description are, however, correct.

Of the many commercial cultivars known to the present inventors the most similar existing cultivars in comparison to Yellow Superstar are the parental cultivar Superstar and Florida Marble (U.S. Plant Pat. No. 3,288). Reference is made to attached Chart A which compares certain characteristics of Yellow Superstar with the same characteristics of Superstar and Florida Marble. General comparisons are as follows:

(1) In comparison to Superstar, Yellow Superstar has different ray floret color, with all other characteristics being similar to those same characteristics of Superstar.

(2) In comparison to Florida Marble, Yellow Superstar has darker yellow ray floret color, larger diameter across face of capitulum, taller plant height, and shorter flowering response period. The branching pattern, capitulum form, and capitulum type of Florida Marble are similar to those same characteristics of Yellow Superstar.

In the following description, color references are made to A Limit Color Cascade by the Munsell Company, 1972 edition. The color values were determined between 3:00 and 3:30 P.M. on Oct. 30, 1978 and between 10:00 and 10:30 A.M. on July 9, 1979. Both observations were made under 200 foot-candle light intensity at Salinas, Calif.

Botanical classification: *Chrysanthemum morifolium,* Ramat., cv Yellow Superstar.

I. Inflorescence:

A. *Capitulum.*—Form: flat. Type: daisy. Diameter across face: 100 to 120 mm.

B. *Corolla of ray florets.*—Color (General Tonality at a distance of 3 feet): Medium yellow 25-5 to 26-4. Color (abaxial): 25-5 to 25-4, (Oct. 30, 1978) ranging to 26-3 (July 9, 1979). Color (adaxial): 25-4 to 25-3.

C. *Corolla of disc florets.*—Color (immature): 20-10. Color (mature): 26-4.

D. *Reproductive organs.*—Androecium: present disc florets only; scant to numerous; scant pollen. Gynoecium: present both ray and disc florets.

II. Plant:

A. *General appearance.*—Semi-upright branching pattern; tall height.

B. *Foliage.*—Color (abaxial): approximately 21-14 to 22-14. Color (adaxial): approximately 21-13 overlaid with white.

CHART A

COMPARISON OF YELLOW SUPERSTAR, SUPERSTAR, AND FLORIDA MARBLE.

| CULTIVAR | RAY FLORET COLOR | DIAMETER ACROSS FACE OF CAPITULUM | PLANT HEIGHT |
|---|---|---|---|
| Yellow Superstar | Medium Yellow | 100 to 120 mm. | Tall, 72 to 82 cm. |
| Superstar | White | 100 to 120 mm. | Tall, 72 to 82 cm. |
| Florida Marble | Light Yellow | 75 to 85 mm. | Medium, 65 to 75 cm. |

CHART A-continued

| CULTIVAR | BRANCHING PATTERN | FLOWERING RESPONSE PERIOD | CAPITULUM FORM AND TYPE |
|---|---|---|---|
| Yellow Superstar | Semi-upright | 7 week | Flat Daisy |
| Superstar | Semi-upright | 7 week | Flat Daisy |
| Florida Marble | Semi-upright | 9 week | Flat Daisy |

COMPARISONS MADE OF NON-PINCHED PLANTS GROWN IN A GREENHOUSE IN SALINAS, CALIFORNIA.

We claim:

1. A new and distinct cultivar of *Chrysanthemum morifolium,* Ramat., known by the cultivar name Yellow Superstar and particularly characterized as to uniqueness by the combined characteristics of daisy capitulum type; flat capitulum form; medium yellow ray floret color; diameter across face of capitulum from 100 to 120 mm. at maturity; uniform seven week photoperiodic flowering response; tall plant height; semi-upright branching pattern; and yellow green (immature) to yellow (mature) disc floret color.

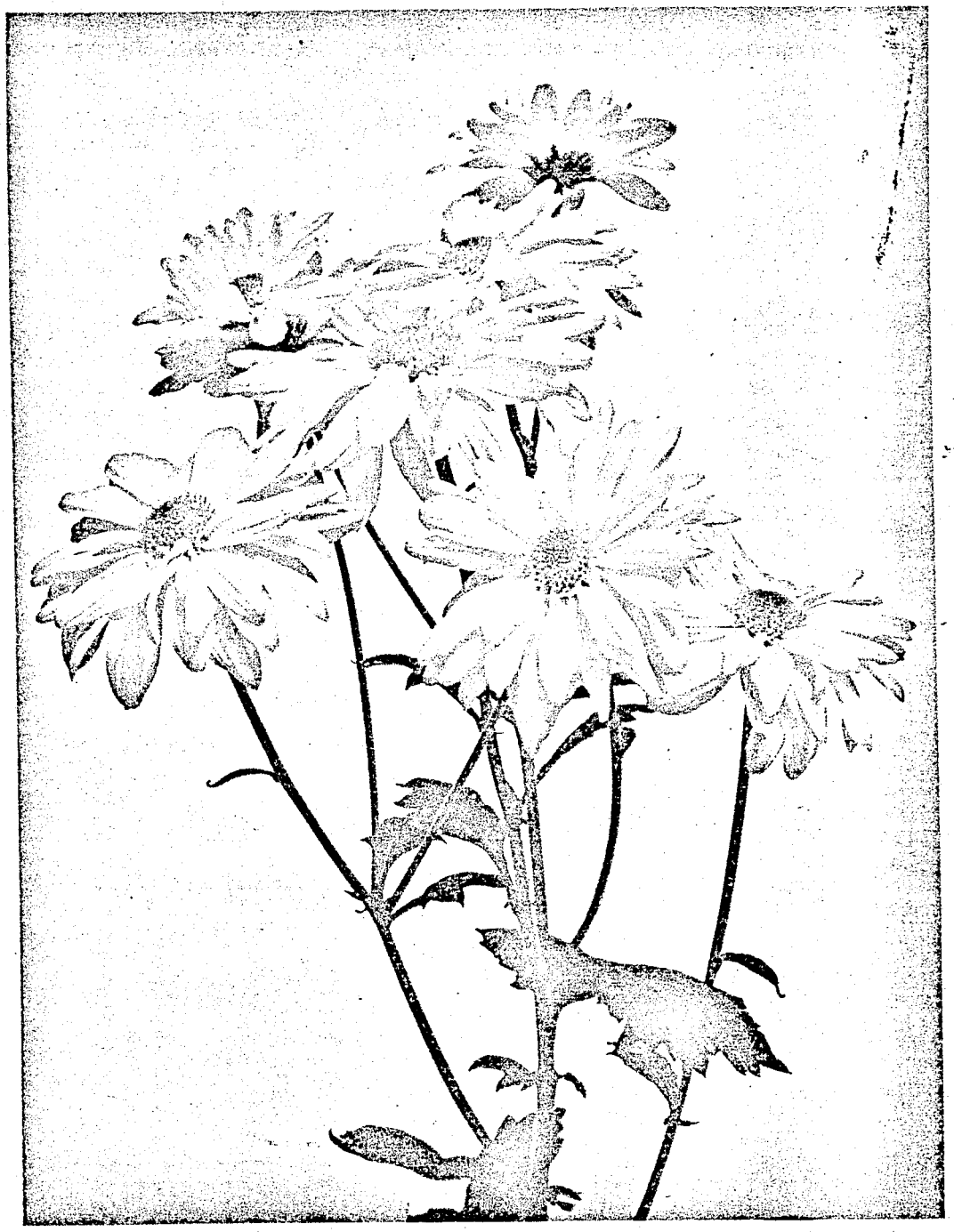

* * * * *